United States Patent
Geurts et al.

[11] Patent Number: 6,117,994
[45] Date of Patent: *Sep. 12, 2000

[54] INTERMEDIATES FOR 16β-METHYL STEROIDS

[75] Inventors: Catherine Geurts, Betz; Michel Vivat, Lagny sur Marne, both of France

[73] Assignee: Hoechst Marion Roussel, France

[*] Notice: This patent is subject to a terminal disclaimer.

[21] Appl. No.: 09/064,576

[22] Filed: Apr. 22, 1998

Related U.S. Application Data

[62] Division of application No. 08/710,198, Sep. 13, 1996, Pat. No. 5,795,982, which is a division of application No. 08/444,229, May 18, 1995, Pat. No. 5,596,108.

[30] Foreign Application Priority Data

Jun. 2, 1994 [FR] France ................... 94 06743

[51] Int. Cl.[7] ............... C07J 3/00; C07J 21/00; C07J 33/00
[52] U.S. Cl. .............. 540/30; 540/36; 552/611
[58] Field of Search .............. 540/30, 34, 36; 552/606, 611, 610

[56] References Cited

U.S. PATENT DOCUMENTS 5,352,809 10/1994 Batist et al. ............ 552/610
5,565,588 10/1996 Batist et al. ............ 552/610

FOREIGN PATENT DOCUMENTS 2199325 7/1988 United Kingdom .

OTHER PUBLICATIONS

Batist et al., Steroids, vol. 55, pp. 109–113, 1990.
Toro et al., "Oxidative decarboxylation of 17(20)–dehydro–23,24–dinorcholanoic acids". Tetrahedron Letters, vol. 31(24), pp. 3475–3476, 1990.

*Primary Examiner*—Shelley A. Dodson
*Assistant Examiner*—Barbara Badio
*Attorney, Agent, or Firm*—Bierman, Muserlian and Lucas

[57] ABSTRACT

A new process for the preparation of 16β-methyl-steroids of the formula

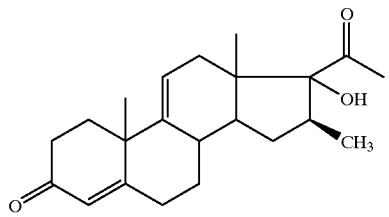

and novel intermediates.

1 Claim, No Drawings

INTERMEDIATES FOR 16β-METHYL STEROIDS

PRIOR APPLICATION

This application is a division of U.S. patent application Ser. No. 08/710,198 filed Sep. 13, 1996, now U.S. Pat. No. 5,795,982 which is a division of U.S. patent application Ser. No. 08/444,229 filed May 18, 1995, now U.S. Pat. No. 5,596,108.

OBJECTS OF THE INVENTION

It is an object of the invention to provide a novel process for the preparation of the 16β-methyl-steroids of formula I and novel intermediates formed therein.

These and other objects and advantages of the invention will become obvious from the following detailed description.

THE INVENTION

The novel process of the invention for the preparation of a 16β-methyl-steroid of the formula

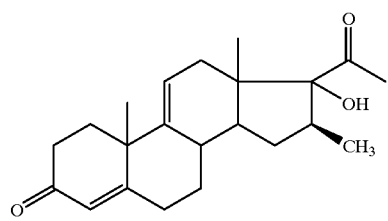

I comprises reacting a compound of the formula

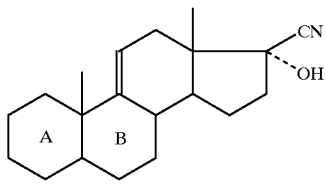

II in which rings A and B are a remainder selected from the group consisting of

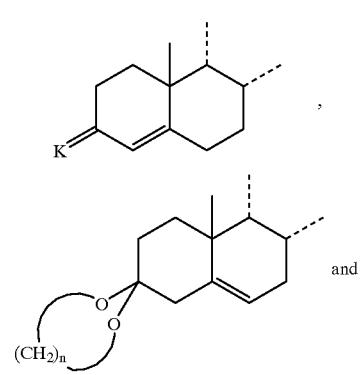

and

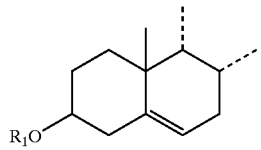

wherein K is oxo or a protector group of an oxo selected from the group consisting of

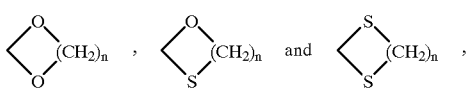

$n$ is 2 or 3 and $R_1$ is an ether or ester residue with a dehydration agent to obtain a compound of the formula

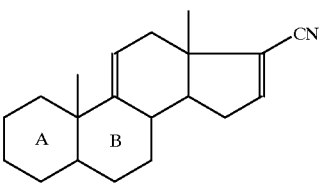

III in which A and B have the above meaning, which, when K is oxo, is reacted with a suitable blocking agent of oxo to obtain the corresponding compound of formula III, in which K has values other than oxo as defined above, reacting the compound of formula III with an organometallic methylation agent to obtain after hydrolysis of the intermediate imine, a methyl ketone of the formula

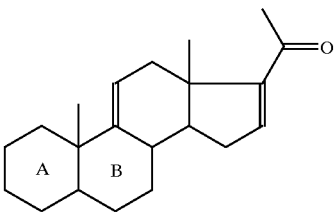

IV reacting the latter in a basic medium with an epoxidation agent to obtain a compound of the formula

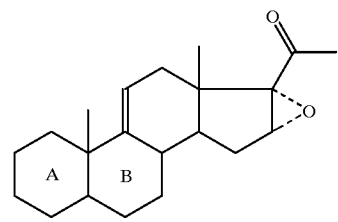

V protecting the 20-keto function to obtain a compound of the formula

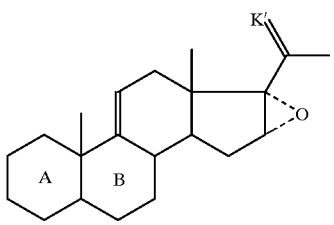

VI in which K' is a protector group of the ketone selected from the group consisting of

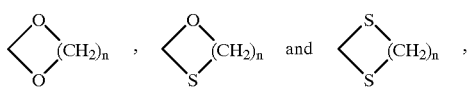

n being defined as previously, reacting the latter with an organometallic methylation agent to obtain the 16β-methyl derivative of the formula

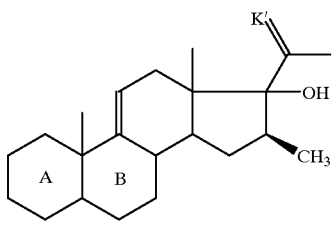

VII unblocking the ketone functions in the 3- and 20 positions to obtain the product of formula I.

When $R_1$ is an ether residue, it can be any residue known to one skilled in the art for blocking 3-position in this form and particularly it can be an alkyl of 1 to 6 carbon atoms, alkoxy-alkoxyalkyl of 3 to 8 carbon atoms, aryl of 6 to 10 carbon atoms or aralkyl of 7 to 12 carbon atoms.

When $R_1$ is alkyl, examples are methyl, ethyl, propyl, isopropyl, n-butyl, sec-butyl, tert-butyl, pentyl or hexyl and when $R_1$ is alkoxyalkoxyalkyl, examples are methoxy-ethoxymethyl.

When $R_1$ is aralkyl, examples are benzyl or phenethyl and when $R_1$ is aryl, examples are phenyl or phenyl substituted by one or more alkyls.

When $R_1$ is an ether residue, it can also be a silylated such as trialkylsilyl like trimethylsilyl, tert-butyl dimethylsilyl or triarylsilyl such as triphenylsilyl or diarylalkylsilyl such as diphenyl tert-butylsiyl.

When $R_1$ is an ester residue, it can be any residue known to one skilled in the art for blocking the 3-position in this form and particularly it can be $-COR_1$, $R_1$ being alkyl, aryl or aralkyl as defined above.

The protection of the 3-ketone function is carried out by methods known to one skilled in the art. Thus, there can be used particularly a mixed diol, dithiol or thiol of the formula HO—$(CH_2)_n$—OH, HS—$(CH_2)_n$—SH or HO—$(CH_2)_n$—SH, in an acid medium, for example in the presence of concentrated hydrochloric acid or hydrobromic acid in catalytic quantity, p-toluene sulfonic acid, or in the presence of a Lewis acid such as zinc chloride, titanium tetrachloride or boron trifluoride, preferably in the form of the etherate. There can also be used methylethyl dioxolane in the presence of an acid, such as one of those named above.

There can also be used alkyl, alkoxyalkoxyalkyl, aralkyl or aryl halide in the presence of a base to intermediately form the enolate, for example a hydride, an alcoholate or an alkali metal hydroxide. There can also be used trialkyl, triaryl or diaryl-alkylsilyl halide in an alkaline medium as above.

There can also be used a suitable acid chloride operating in the presence of a base, which can be a nitrogenous base such as triethylamine, pyridine, dimethylaminopyridine or a mineral base, particularly a hydride, an alcoholate or an alkalimetal hydroxide.

The dehydration agent is preferably phosphorus oxychloride, preferably in the presence of a tertiary amine such as pyridine. There can also be used a Lewis acid such as ferric chloride, boron trifluoride and its complexes, for example the etherate, titanium tetrachloride, aluminum chloride or tin chloride, a mineral acid such as sulfuric acid, a sulfonic acid such as p-toluene sulfonic acid or chlorosulfonic acid or a derivative such as methane sulfonyl chloride.

The organometallic methylation agent producing the methyl-ketone is for example a magnesium compound, a lithium compound, a cadmium compound or a derivative of copper such as $CH_3Cu$, $(CH_3)_2CuMg$ or $(CH_3)_2CuLi$. A magnesium compound such as methylmagnesium halide or methyllithium is preferred. The operation is carried out in a solvent which is preferably an ether such as ethyl ether, tetra-hydrofuran or dioxane, but can also be an aromatic solvent such as toluene or xylene. The operation can also be carried out in an ether-aromatic solvent mixture.

The hydrolysis of the intermediately-formed imine is carried out using an aqueous acid, for example acetic acid, formic acid or a mineral acid such as hydrochloric acid.

The epoxidation agent can be a peracid such as m-chloroperbenzoic acid, perphthalic acid, pertungstic acid or hydrogen peroxide used alone or in the presence of hexachloro- or hexa-fluoroacetone. The epoxidation agent can also be a hydroperoxide such as tertbutyl hydroperoxide used in the presence of vanadium acetyl acetonate or other metals such as molybdenum, in catalytic quantity. Hydrogen peroxide is more preferred. The operation is carried out in a slightly basic medium, either in the presence of a base, for example sodium hydroxide, or in a medium buffered, for example, with sodium acetate, disodium phosphate or sodium bicarbonate or by a trisodium phosphate—phosphoric acid mixture. The operation is carried out in an organic solvent such as methylene chloride, carbon tetrachloride, chloroform, methanol, tetrahydrofuran, dioxane, toluene, ethyl acetate or a mixture of these solvents, if appropriate in the presence of water.

The protection of the 20-keto function is in the form of a ketal, mixed ketal or dithioketal by methods known to a man skilled in the art. Thus, there can be used a mixed diol, dithiol or thiol of the formula HO—$(CH_2)_n$—OH, HS—$(CH_2)_n$—SH or HO—$(CH_2)_n$—SH, in an acid medium, for example in the presence of concentrated hydrochloric or hydrobromic acid in catalytic quantity, p-toluene sulfonic acid, or in the presence of a Lewis acid such as zinc chloride, titanium tetrachloride or boron trifluoride, preferably in the form of the etherate.

The organometallic methylation agent which is reacted with the epoxide of formula VI is one of those which have been mentioned above, the preferred agents also being those which have been mentioned such as those above.

The release of the ketone functions in 3- and 20-positions is effected by means appropriate to the nature of the protector group. An acid agent in the presence of water or a water—alkanol mixture is used in the case of a ketal. It is for example a mineral or organic acid such as hydrochloric acid, hydrobromic acid, sulfuric acid, perchloric acid, nitric acid, p-toluene sulfonic acid, acetic acid, formic acid, oxalic acid or a mixture of acids, or also an acid resin, for example a sulfonic acid resin. In the case of a thioketal or a mixed ketal, the deprotection is carried out by the action of iodine in the presence of a base, for example an alkali-metal bicarbonate, or by the action of iodine in catalytic quantity, in the presence of an oxidizing agent, particularly hydrogen peroxide, by the action of methyl iodide, glyoxylic acid, or the salts of metals such as mercury, cadmium, copper or silver. The operation can generally be carried out in a solvent such as a lower alkanol like methanol or ethanol, mixed with a halogenated solvent, for example methylene chloride in the presence of water. In the case of a mixed ketal, deprotection is also carried out for example with a mercuric salt such as mercuric chloride in the presence of an acetic acid/potassium acetate buffer at about 100° C., with Raney nickel under the same conditions as above or with a hot hydrochloric acid—acetic acid mixture.

In the case where $R_1$ is an ether or ester residue, an acid treatment is also used, particularly under the conditions described above for the ketal.

A preferred process is characterized in that the compound of formula II used is one in which rings A and B are the remainder

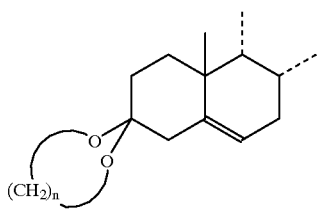

n being defined as previously and particular is 2 and that wherein the 20-keto function is protected by the same ketal as in 3-position and particularly by ethylenedioxy.

The novel intermediates of the invention are the product of formula III, in which K has the definitions indicated previously with the exception of oxo as well as the products of formulae IV, V, VI and VII as defined previously.

The starting compounds of the formula II are known and can be prepared from the 3-keto compound described in European patent No. 263,569 or by the process described in French patent No. 1,079,781, East German patent No. 281,394 or WO application No. 88-03534.

The compound of formula I is an important intermediate for the synthesis of betamethasone as described in European patent No. 54,810.

In the following Examples, there are described several preferred embodiment to illustrate the invention. However, it should be understood that the invention is not intended to be limited to the specific embodiments.

EXAMPLE

16β-methyl-$\Delta^{4,9(11)}$-pregnadiene-17α-ol-3,20-dione

Stage A: cyclic 3-(1,2-ethanediyl)-acetal of 17-cyano-$\Delta^{5,9(11),16(17)}$-androst-trien-3-one 30 g of cyclic 3-(1,2-ethanediyl)-acetal of 17β-cyano-$\Delta^{5,9(11)}$-androst-dien-17α-ol-3-one and 240 ml of anhydrous pyridine were mixed together under an inert gas atmosphere and then 30 ml of phosphorus oxychloride were added. The reaction medium was stirred for 2 hours in an oil bath at 40° C. and then for 18 hours at 45° C. The mixture was poured into a mixture of 450 g of ice, 240 ml of hydrochloric acid at 22° Be and 100 ml of water. The mixture was stirred at ambient temperature followed by separation, and the crystals were washed with water, then dried. The crude product was suspended in an isopropyl ether—isopropanol mixture (2-1) and then the crystals were separated and dried to obtain 24.27 g of the expected product melting at 205–208° C.

IR spectrum: (CHCl$_3$); Absorptions at 2217 cm$^{-1}$ (CN), 1660, 1630 and 1593 cm$^{-1}$ (C=C). NMR spectrum: (CDCl$_3$+C$_5$D$_5$N—300 MHz-ppm); 0.91 (s): 18-CH$_3$; 1.23 (s): 19-CH$_3$; 3.96: ketal; 5.44 (m)-5.45 (m): H$_6$ and H$_{11}$; 6.65: H$_{16}$.

Stage B: cyclic 3-(1,2-ethanediyl)-acetal of $\Delta^{5,9(11),16(17)}$-pregna-triene-3,20-dione 9 g of the product of Stage A and 27 ml of toluene were mixed together under an inert gas atmosphere and then 27 ml of a 3M solution of methylmagnesium chloride in tetrahydrofuran were introduced. The reaction medium was taken to 60/65° C. for 3 hours 30 minutes and then cooled using an ice-methanol bath. 36 ml of tetrahydrofuran were added and then the mixture was poured, under a nitrogen pressure at 10° C. maximum, into a mixture of 81 ml of ice, 27 ml of water and 135 ml of acetic acid cooled in an ice-methanol bath. The temperature was allowed to rise to about 20° C. and concentration was carried out under reduced pressure by gently heating with a water bath at 45° C. Then, the reaction medium was poured into 20 volumes of a water and ice mixture. The temperature was allowed to rise with stirring and then the crystals were separated, washed with water and dried to obtain 9.03 g of crude product which was impasted in a mixture of 45 ml of methanol, 5 ml of water and 0.5 ml of triethylamine. After heating at reflux for 90 minutes, then cooling down to ambient temperature, the crystals were separate, washed with methanol with 10% water and dried to obtain 7.12 g of the expected product melting at 217–219° C.

IR spectrum: (CHCl$_3$); Absorptions at 1664, 1590, 1361 cm$^{-1}$: unsaturated, α, β-methyl ketone. NMR spectrum: (CDCl$_3$+C$_5$D$_5$N—300 MHz-ppm); 0.87 (s): 18-CH$_3$; 1.22 (s): 19-CH$_3$; 2.26 (s): methyl-ketone; 3.94 (m): ketal; 5.44–5.45 (m): —CH= in positions 11 and 5; 6.71 (t): —CH= in position 16.

Stage C: cyclic 3-(1,2-ethanediyl)-acetal of 16α,17α-epoxy-$\Delta^{5,9(11)}$-pregna-diene-3,20-dione 7 g of the product of Stage B, 70 ml of tetrahydrofuran and 35 ml of methanol were mixed together under an inert gas atmosphere and 7 ml of concentrated sodium hydroxide and 7 ml of hydrogen peroxide 200 volumes were introduced. The reaction medium was heated at 40/45° C. for 17 hours and then cooled to ambient temperature and poured into a mixture of 70 ml of water and 70 g of ice. The mixture was stirred while allowing the temperature to rise. Then, separation was carried out, followed by washing with water at the end of the oxidizing power and drying to obtain 7.08 g of the expected product which was used as is for the following stage.

IR spectrum: (CHCl$_3$); Absorptions at 1704 (C=O), 901–855 cm$^{-1}$ (epoxide). NMR spectrum: (CDCl$_3$+C$_5$D$_5$N—300 MHz-ppm) 1.00 (s): 18-CH$_3$; 1.20 (s): 19-CH$_3$; 2.04 (s): methyl-ketone; 3.74 (s): —CH= in position 16; 3.94 (m): ketal; 5.40 (m) 5.51 (t): —CH= in positions 11 and 5.

Stage D: cyclic 3,20-bis-(1,2-ethanediyl)-acetal of 16α,17α-epoxy $\Delta^{5,9(11)}$-pregnadiene-3,20-dione 4 g of the product of Stage C, 40 ml of methylene chloride, 40 ml of ethylene glycol, 20 ml of ethyl orthoformate and 0.3 g of dihydrated p-toluene sulfonic acid were mixed together under an inert gas atmosphere. After 7 hours, concentration was carried out at a reduced pressure of 1 mbar at ambient temperature and then the reaction medium was stirred for 30 minutes. The mixture was poured into 300 ml of a 10% aqueous solution of sodium bicarbonate and then degassed for 30 minutes. After separation, the crystals were washed with water and then dried. The product was purified by chromatography on silica eluting with a toluene—ethyl acetate mixture (8-2) with 0.05% of triethylamine and the product obtained was taken up in cyclohexane, separated and dried under reduced pressure to obtain 3.28 g of the expected product melting at 176–177° C.

IR spectrum: (CHCl$_3$); Absence of C=O. Presence of ketal. NMR spectrum: (CDCl$_3$+C$_5$D$_5$N—300 MHz-ppm); 0.94 (s): 18-CH$_3$; 1.20 (s): 19-CH$_3$; 1.42 (s): CH$_3$—; 3.41 (s): H in position 16; 3.85 to 4.05: ketal; 5.41 and 5.48: H in position 6 and H in position 11.

Stage E: cyclic 3,20-bis-(1,2-ethanediyl)-acetal of 16β-methyl-$\Delta^{5,9(11)}$-pregnadiene-17α-ol-3,20-dione 24 ml a 3M solution of methyl magnesium bromide in ether were ice-cooled under an inert gas atmosphere and the solvent was evaporated under reduced pressure and by warming with a bath at 60/65° C. Then, 21 ml of tetrahydrofuran and 3 g of the product of Stage D were introduced and the mixture was stirred for 16 hours while taking the temperature of the bath to 70° C. 4 ml of an ethereal solution of the above magnesium compound and 10 ml of tetrahydrofuran were added and the mixture was stirred for 7 hours. A further 10 ml of tetrahydrofuran were added and the mixture was refluxed for 16 hours, then cooled to 40° C. and poured into a mixture maintained at 0° C. of 16 g of dehydrated sodium acid phosphate and 900 ml of water. The temperature was allowed to rise and then separation was carried out. The product was washed with water and dried. The product was purified by impasting in 15 volumes of a methylene chloride—ethyl acetate mixture (9-1) with 0.05% of triethylamine and then by chromatography on silica, eluting with the same mixture to obtain 2.42 g of the expected product melting at 180–181° C.

IR Spectrum: (CHCl$_3$); Absorptions at 3580 cm$^{-1}$: OH; 1670–1644 cm$^{-1}$: C=C. NMR spectrum: (CDCl$_3$+C$_5$D$_5$N—300 MHz-ppm); 0.87 (s): 18—CH$_3$; 1.19 (d): CH$_3$—CH—; 1.20 (s): 19—CH$_3$; 1.39 (s): CH$_3$—C—; 3.85 to 4.05: ketals; 5.45 and 5.48: H in position 6 and H in position 11.

Stage F: 16β-methyl-$\Delta^{4,9(11)}$-pregnadiene-17α-ol-3,20-dione 2 g of the product of Stage E, 15 ml of acetone and 5 ml of water were mixed together under an inert gas atmosphere and 4 drops of concentrated sulfuric acid were introduced. The mixture was heated for 4 hours 30 minutes in a bath at 60° C. and then 20 ml of water were added. The reaction medium was allowed to cool and the crystals were separated and washed with water, then dried to obtain 1.55 g of the expected product melting at 173° C.

IR spectrum: (CHCl$_3$); Absorptions at 3610 cm$^{-1}$: —OH; 1709–1353 cm$^{-1}$: CO—CH$_3$; 1663–1616 cm$^{-1}$: 3$\Delta$4 keto. NMR spectrum: (CDCl$_3$—300 MHz-ppm); 87 (s): 18-CH$_3$; 1.19 (d, J=7): CH$_3$—CH—; 1.34 (s): 19-CH$_3$; 2.27 (s): —CO—CH$_3$; 3.01 (s): 1H mobile; 5.52 (m): H in position 11; 5.75 (m): H in position 4.

Various modifications of the process and intermediates of the invention may be made without departing from the spirit or scope thereof and it is to be understood that the invention is intended to be limited only as defined in the appended claims.

What we claim is:
1. A compound of the formula

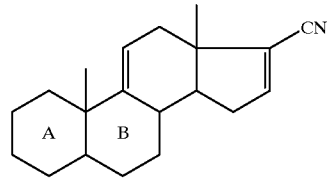

wherein A and B are selected from the group consisting of

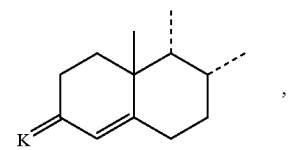

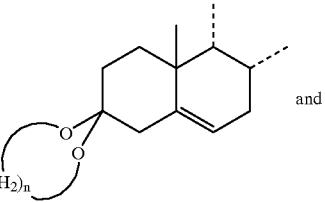

and

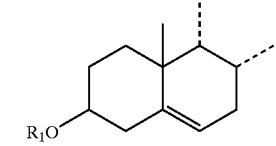

K is selected from the group consisting of

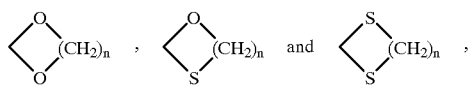

n is 2 or 3 and R$_1$ is an ether or ester residue.

* * * * *